(12) United States Patent
Fatemi et al.

(10) Patent No.: US 12,343,204 B2
(45) Date of Patent: Jul. 1, 2025

(54) SYSTEMS AND METHODS FOR LOCALIZING A MEDICAL DEVICE USING SYMMETRIC DOPPLER FREQUENCY SHIFTS MEASURED WITH ULTRASOUND IMAGING

(71) Applicant: Mayo Foundation for Medical Education and Research, Rochester, MN (US)

(72) Inventors: Mostafa Fatemi, Rochester, MN (US); Azra Alizad, Rochester, MN (US); Marek Belohlavek, Scottsdale, AZ (US); Viksit Kumar, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 18/188,308

(22) Filed: Mar. 22, 2023

(65) Prior Publication Data
US 2023/0240649 A1 Aug. 3, 2023

Related U.S. Application Data

(62) Division of application No. 16/577,194, filed on Sep. 20, 2019, now Pat. No. 11,642,100.
(Continued)

(51) Int. Cl.
*A61B 8/00* (2006.01)
*A61B 5/00* (2006.01)
(Continued)

(52) U.S. Cl.
CPC .......... *A61B 8/4245* (2013.01); *A61B 8/0841* (2013.01); *A61B 8/4488* (2013.01);
(Continued)

(58) Field of Classification Search
None
See application file for complete search history.

(56) References Cited

U.S. PATENT DOCUMENTS

| | | | |
|---|---|---|---|
| 4,217,684 A | 8/1980 | Brisken | |
| 4,249,539 A | 2/1981 | Vilkmerson | |
| (Continued) | | | |

FOREIGN PATENT DOCUMENTS

| | | |
|---|---|---|
| EP | 1132049 A1 | 9/2001 |
| FR | 2716266 A1 | 8/1995 |
| (Continued) | | |

OTHER PUBLICATIONS

Anagnostopoulos PC, et al. (2002). "Epicardial ultrasound guidance of coronary catheter placement in an experimental animal model." J Am Soc Echocardiogr 15:1387-90.
(Continued)

*Primary Examiner* — Jason M Ip
*Assistant Examiner* — Renee C Langhals
(74) *Attorney, Agent, or Firm* — Quarles & Brady LLP

(57) ABSTRACT

Described here are systems and method for using ultrasound to localize a medical device to which an active ultrasound element that can transmits ultrasound energy is attached. Doppler signal data of the medical device are acquired while the active element is transmitting acoustic energy, and the Doppler signal data are processed to detect symmetric Doppler shifts associated with the active element. The systems and methods described in the present disclosure enable tracking and display of one or more locations on or associated with the medical device.

2 Claims, 5 Drawing Sheets

Related U.S. Application Data

(60) Provisional application No. 62/733,931, filed on Sep. 20, 2018.

(51) Int. Cl.
*A61B 8/08* (2006.01)
*A61B 34/20* (2016.01)
*A61B 90/00* (2016.01)

(52) U.S. Cl.
CPC .............. *A61B 8/488* (2013.01); *A61B 90/37* (2016.02); *A61B 5/7257* (2013.01); *A61B 2034/2063* (2016.02); *A61B 2090/364* (2016.02); *A61B 2090/378* (2016.02)

(56) References Cited

U.S. PATENT DOCUMENTS

| | | | |
|---|---|---|---|
| 4,425,525 | A | 1/1984 | Smith |
| 4,431,006 | A | 2/1984 | Trimmer |
| 4,441,503 | A | 4/1984 | O'Donnell |
| 4,470,305 | A | 9/1984 | O'Donnell |
| 4,569,231 | A | 2/1986 | Carnes |
| 4,697,595 | A | 10/1987 | Breyer |
| 4,706,681 | A | 11/1987 | Breyer |
| 5,158,088 | A | 10/1992 | Nelson |
| 5,161,536 | A | 11/1992 | Vilkomerson |
| 5,329,927 | A | 7/1994 | Gardineer |
| 5,588,432 | A | 12/1996 | Crowley |
| 5,830,144 | A | 11/1998 | Vesely |
| 5,840,030 | A | 11/1998 | Ferek-Petric |
| 5,840,031 | A | 11/1998 | Crowley |
| 6,004,269 | A | 12/1999 | Crowley |
| 6,612,992 | B1 | 9/2003 | Hossack |
| 7,280,863 | B2 | 10/2007 | Shachar |
| 7,686,767 | B2 | 3/2010 | Maschke |
| 8,956,300 | B2 | 2/2015 | Guo |
| 9,289,185 | B2 | 3/2016 | Mung |
| 9,622,719 | B2 | 4/2017 | Maizes |
| 2003/0036696 | A1 | 2/2003 | Willis |
| 2007/0167822 | A1 | 7/2007 | Webler |
| 2007/0213616 | A1 | 9/2007 | Anderson |
| 2008/0275380 | A1 | 11/2008 | Hennings |
| 2009/0005675 | A1 | 1/2009 | Grunwald |
| 2009/0118612 | A1 | 5/2009 | Grunwald |
| 2011/0160592 | A1 | 6/2011 | Mitchell |
| 2011/0295108 | A1 | 12/2011 | Cox |
| 2013/0165788 | A1 | 6/2013 | Osumi et al. |
| 2013/0204138 | A1* | 8/2013 | Belohlavek ............ A61B 8/445 600/463 |
| 2015/0045666 | A1* | 2/2015 | Lin ...................... A61B 8/5223 600/441 |
| 2016/0324501 | A1 | 11/2016 | Vignon et al. |
| 2018/0000446 | A1 | 1/2018 | Lu et al. |
| 2018/0235576 | A1* | 8/2018 | Brannan ................ A61B 8/488 |
| 2019/0015052 | A1 | 1/2019 | Scalzo |
| 2019/0142528 | A1 | 5/2019 | Vertikov |

FOREIGN PATENT DOCUMENTS

| | | |
|---|---|---|
| WO | 2012024201 A1 | 2/2012 |
| WO | 2014207666 A1 | 12/2014 |

OTHER PUBLICATIONS

Armstrong, et al., Localization of Needle Tip with Color Doppler During Pericardiocentesis: In Vitro Validation and Initial Clinical Application, Journal of the American Society of Echocardiography, 2001, 14:29-37.

Asanuma T, et al (2001). "Radiofrequency spectral analysis of attenuated ultrasound signals in experiments with echo contrast microbubbles." J Am Soc Echocardiogr 14:789-97.

Asanuma T, et al (2002). "Radio frequency dual-spectra analysis of regional myocardial perfusion." J Am Soc Echocardiogr 15:1277-84.

Belohlavek M, et al (2001). "Vibro-acoustography: quantification of flow with highly-localized low-frequency acoustic force." Ultrason Imaging 23:249-56.

Belohlavek M, et al (1993). "Three- and four-dimensional cardiovascular ultrasound imaging." Mayo Clin Proc 68:221-40.

Belohlavek M, et al (1994). "Diagnostic performance of two-dimensional versus three-dimensional transesophageal echocardiographic images of selected pathologies evaluated by receiver operating characteristic analysis." Echocardiography 11 :635-45.

Belohlavek M, et al. A real-time color Doppler marker for echocardiographic guidance of an acoustically active extracorporeal membrane oxygenation cannula. J Ultrasound Med 2018. PMID: 30419612. In Process in NIHMS, NIHMSID: 1006726.

Belohlavek M, et al (1996). "Extraction of endocardial boundary from echocardiographic images by means of the Kohonen self-organizing map." Acoustical Imaging. Plenum Press 22:197-202.

Belohlavek M, et al. "Acoustically active injection catheter guided by ultrasound: navigation tests in acutely ischemic porcine hearts." Ultrasound in medicine & biology 40.7 (2014): 1650-1659.

Bjaerum S, et al (2002). "Clutter filter design for ultrasound color flow imaging." IEEE Trans Ultrason Ferroelectr Freq Control 49:204-16.

Censor D., "Harmonic and transient scattering from time varying obstacles.," Journal of the Acoustical Society of America, vol. 76, pp. 1527-1534, 1984.

Censor D., "Scattering by time varying obstacles.," Journal of Sound and Vibration, vol. 25, pp. 101-110, 1972.

Censor D., et al., "Theory of ultrasound Doppler-spectra velocimetry for arbitrary beam and flow configurations," IEEE Transactions on Biomedical Engineering, vol. 35, pp. 740-751, Sep. 1988.

Fatemi M et al.(1998). "Ultrasound-stimulated vibroacoustic spectrography." Science 280:82-5.

Fronheiser, et al., Real-Time 3D Color Doppler for Guidance of Vibrating Interventional Devices, 2004 IEEE Ultrasonics Symposium, 1:149-152.

Fronheiser, et al., Vibrating Interventional Device Detection Using Real-Time 3-D Color Doppler, IEEE Transactions on Ultrasonics, Ferroelectrics, and Frequency Control, 2008, 55(6):1355-1362.

Heimdal A et al (1997). "Ultrasound Doppler measurements of low velocity blood flow: limitations due to clutter signals from vibrating muscles." IEEE Trans Ultrason Ferroelec Freq Control 44:873-881.

Jensen JA (1991 ). "A model for the propagation and scattering of ultrasound in tissue." J Acoust Soc Am 89:182-90.

Karmarkar PV, et al.(2004). "MR-trackable intramyocardial injection catheter." Magn Reson Med 51:1163-72.

Katayama, M., et al. "Acoustically active catheter for intracardiac navigation by color Doppler ultrasonography." Ultrasound in medicine & biology 43.9 (2017): 1888-1896.

Kenny A, et al (1994). "Measurement of left anterior descending coronary artery flow velocities by transthoracic Doppler ultrasound." Am J Cardiol 73:1021-2.

Korinek J, et al. Does implantation of sonomicrometry crystals alter regional cardiac muscle function? J Am Soc Echocardiogr 2007;20:1407-12. PMID: 17604963.

Kumar V, et al. Unambiguous identification and visualization of an acoustically active catheter by ultrasound imaging in real time: theory, algorithm, and phantom experiments. IEEE Trans Biomed Eng 2018;65:1468-1475. PMID: 28952929. PMC5999572.

Kumar, V., et al. "Real-Time Visualization of an Acoustically Active Injection Catheter With Ultrasound Imaging: Algorithm and In Vivo Validation in a Swine Model." IEEE Transactions on Biomedical Engineering 66.11 (2019): 3212-3219.

Langberg JJ, et al. The echo-transponder electrode catheter: a new method for mapping the left ventricle. J Am Coll Cardiol 1988;12:218-223. PMID: 3379208.

Lloyd-Jones OM, et al.(2002). "Lifetime risk for developing congestive heart failure: the Framingham study." Circulation 106:3068-3072.

(56) References Cited

OTHER PUBLICATIONS

Losordo DW, et al. Intramyocardial, autologous CD34+ cell therapy for refractory angina. Circ Res 2011;109:428-36. PMID: 21737787.

McMahon, E. M., et al. "Accurate guidance of a catheter by ultrasound imaging and identification of a catheter tip by pulsed-wave Doppler." Pacing and clinical electrophysiology 35.1 (2012): 44-50.

PCT International Search Report and Written Opinion, PCT/US2011/047711, Dec. 16, 2011.

Pizzuto F, et al (2003). "Noninvasive coronary flow reserve assessed by transthoracic coronary Doppler ultrasound in patients with left anterior descending coronary artery stents." Am J Cardiol 91:522-6.

Rodriguez-Parcel M, et al (2008). "Reporter gene imaging following percutaneous delivery in swine moving toward clinical applications." J Am Coll Cardiol 51:595-7.

Sikdar S, et al (2004). "Ultrasonic techniques for assessing wall vibrations in stenosed arteries." Conf Proc IEEE Eng Med Biol Soc 2: 1325-8.

Sikdar S, et al (2007). "Ultrasonic Doppler vibrometry." J Am Soc Echocardiogr 20:1386-92.

Vilkomerson D, et al. A system for ultrasonic beacon-guidance of catheters and other minimally-invasive medical devices. IEEE Trans Ultrason Ferroelectr Freq Control 1997;44:496-504. PMID: 18244147.

Voci P, et al (2003). "Usefulness of coronary flow reserve measured by transthoracic coronary Doppler ultrasound to detect severe left anterior descending coronary artery stenosis." Am J Cardiol 92:1320-4.

Von Bibra H, et al (1999). "Interaction of Microbubbles with Ultrasound." Echocardiography 16:733-741.

Wada N, et al (2005). "Comparison of high-frequency two-dimensional transthoracic echocardiography versus intravascular ultrasound for evaluation of the left anterior descending coronary artery." Am J Cardiel 96:1746-9.

Wang J, et al (2005). "Delayed onset of subendocardial diastolic thinning at rest identifies hypoperfused myocardium." Circulation 111:2943-50.

Wang J, et al (2005). "Direct identification of subendocardial postsystolic thickening by intracardiac M-mode Doppler echocardiography." Echocardiography 22:145-7.

Wang J, et al (2006). "Analysis of postsystolic myocardial thickening work in selective myocardial layers during progressive myocardial ischemia." J Am Soc Echocardiogr 19:1102-11.

Williams AR, et al. Intramyocardial stem cell injection in patients with ischemic cardiomyopathy: functional recovery and reverse remodeling. Circ Res 2011;108:792-6. PMID: 21415390.

Winsberg F, et al. Use of an acoustic transponder for US visualization of biopsy needles. Radiology 1991;180:877-8. PMID: 1871312.

Wunenburger, R. et al., "Experimental study of the Doppler shift generated by a vibrating scatterer," Journal of the Acoustical Society of America, vol. 115, pp. 507-514, Feb. 2004.

Yoshifuku S, et al (2007a). "Parametric detection and measurement of perfusion defects in attenuated contrast echocardiographic images." J Ultrasound Med 26:739-48.

Yoshifuku S, et al (2007b). "Parametric harmonic-to-fundamental ratio contrast echocardiography: a novel approach to identification and accurate measurement of left ventricular area under variable levels of ultrasound signal attenuation." Ultrasonics 46:109-18.

\* cited by examiner

SYSTEMS AND METHODS FOR LOCALIZING A MEDICAL DEVICE USING SYMMETRIC DOPPLER FREQUENCY SHIFTS MEASURED WITH ULTRASOUND IMAGING

CROSS-REFERENCE TO RELATED APPLICATIONS

This application is a divisional of U.S. patent application Ser. No. 16/577,194, filed on Sep. 20, 2019, which claims the benefit of U.S. Provisional Patent Application Ser. No. 62/733,931, filed on Sep. 20, 2018, and entitled "SYSTEMS AND METHODS FOR LOCALIZING A MEDICAL DEVICE USING SYMMETRIC DOPPLER FREQUENCY SHIFTS MEASURED WITH ULTRASOUND IMAGING," which is herein incorporated by reference in its entirety.

STATEMENT REGARDING FEDERALLY SPONSORED RESEARCH

This invention was made with government support under EB019947 awarded by the National Institutes of Health. The government has certain rights in the invention.

BACKGROUND

Minimally invasive procedures are rapidly replacing conventional invasive surgery due to smaller incisions, less scar tissue, lower risk of infection, shorter hospitalization, and faster recovery time. Ultrasound imaging has been used for guidance of minimally invasive procedures for years and has advanced by employing 3D cardiac ultrasound for guiding deployment of valve prostheses and closure devices.

Despite these advances, challenges with sound propagation and ultrasound image artifacts impede guidance and exact targeting of catheters for investigative (e.g., electrophysiology), diagnostic (e.g., biopsy), or therapeutic (e.g., drug delivery of cellular or molecular therapy) purposes. Traditional invasive devices can be difficult to locate with pulse echo ultrasound due to the specular nature of the invasive device. In order to better visualize the invasive device, hyperechoic needles with a screw have been used to increase the number of reflective surfaces. However this approach does not aid in identifying the tip of the needle, and improvement in visualization is also limited.

Angiography and other fluoroscopic techniques provide planar projection of complex 3D organs with limited visualization of anatomy. One advantage of guidance by ultrasound is in navigating the catheter along with real-time depiction of its surrounding anatomy. Additional benefits include simultaneous Doppler analysis of blood flow through vasculature, cardiac cavities, and valves, as well as portability, cost effectiveness, and wide availability.

Ultrasound guidance methods are not without their own challenges. For example, the catheter tip can be confused with other parts of the catheter shaft within an ultrasound image plane. The catheter could also have the same level of brightness as the surrounding anatomy (i.e., ultrasonography may not resolve all possible image ambiguities arising from the B-mode image). Some of the uncertainty between identification of catheter versus anatomy can be overcome by controlled movement of the catheter by the user.

SUMMARY OF THE DISCLOSURE

The present disclosure addresses the aforementioned drawbacks by providing a method for localizing a medical device using an ultrasound imaging system. Doppler signal data are acquired. The Doppler signal data are representative of a medical device having coupled thereto an active element that is transmitting acoustic energy at a frequency while the Doppler signal data are acquired. Spectral data are generated by computing a Fourier transform of the Doppler signal data. A positive Doppler shift threshold value is computed based on a signal-to-noise ratio of the spectral data in a window centered on a positive Doppler shift associated with the frequency of the active element. A negative Doppler shift threshold value is computed based on a signal-to-noise ratio of the spectral data in a window centered on a negative Doppler shift associated with the frequency of the active element. Spatial locations are identified as being associated with a location of the active element by thresholding the Doppler signal data using the positive Doppler shift threshold value and the negative Doppler shift threshold value. A display that provides a visual depiction of the spatial locations associated with the location of the active element is then generated.

It is another aspect of the present disclosure to provide a method for localizing a medical device using an ultrasound imaging system. Doppler signal data are acquired. The Doppler signal data are representative of a medical device having coupled thereto an active element that is transmitting acoustic energy at a frequency while the Doppler signal data are acquired. Time domain signal data are generated with a computer system based on the Doppler signal data. Positive Doppler shifts and negative Doppler shifts are each isolated in the time domain data using the computer system. Spatial locations are identified as being associated with a location of the active element by implementing a mean frequency estimator with a hardware processor and a memory of the computer system, wherein the mean frequency estimator takes as an input the isolated positive Doppler shifts and the isolated negative Doppler shifts. A display that provides a visual depiction of the spatial locations associated with the location of the active element is then generated.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Figure 1:
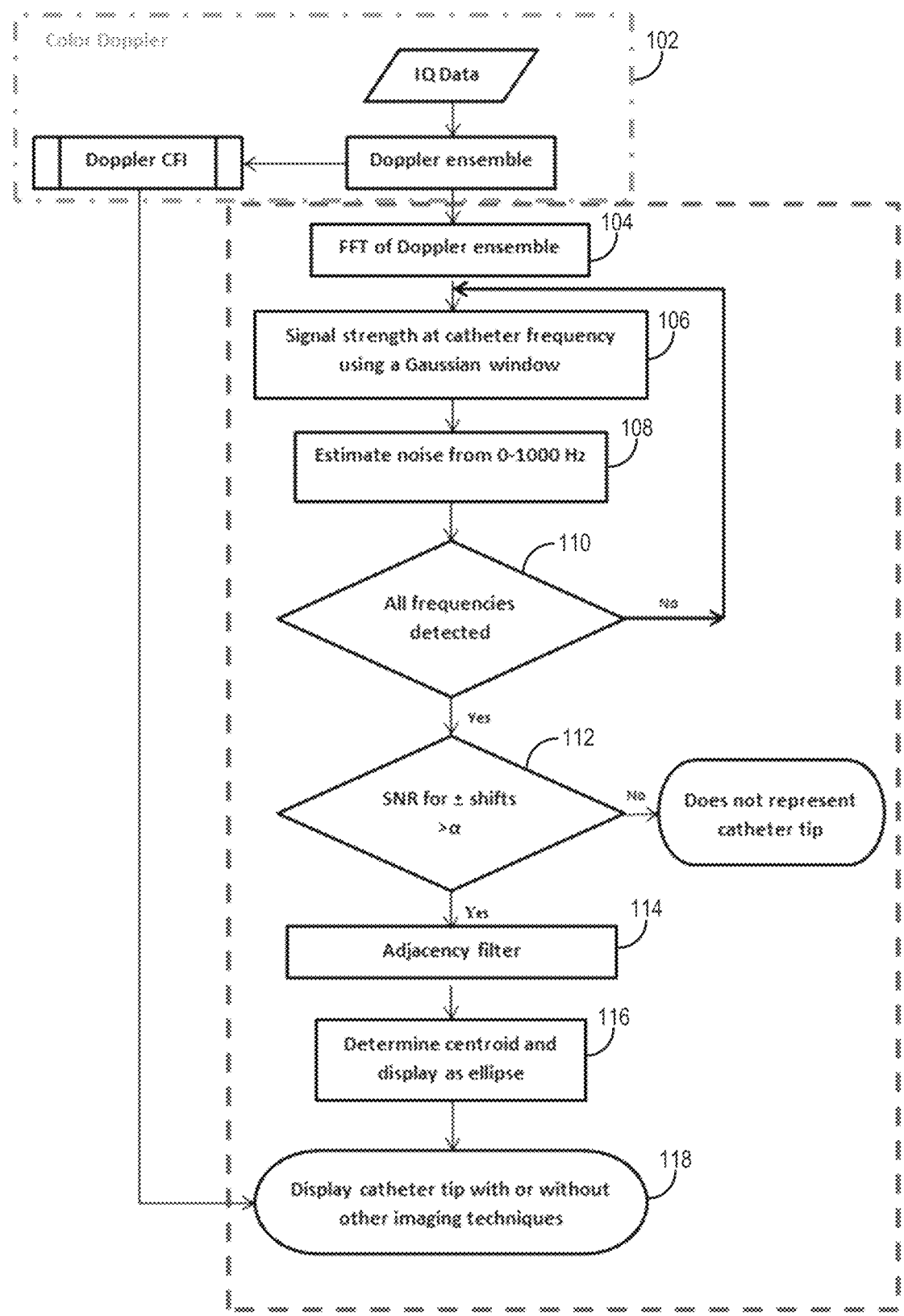
FIG. 1 is a flowchart setting forth the steps of an example method for localizing and/or tracking a medical device based on symmetric Doppler shifts measured with an ultrasound imaging system using a frequency domain approach.
Figure 2:
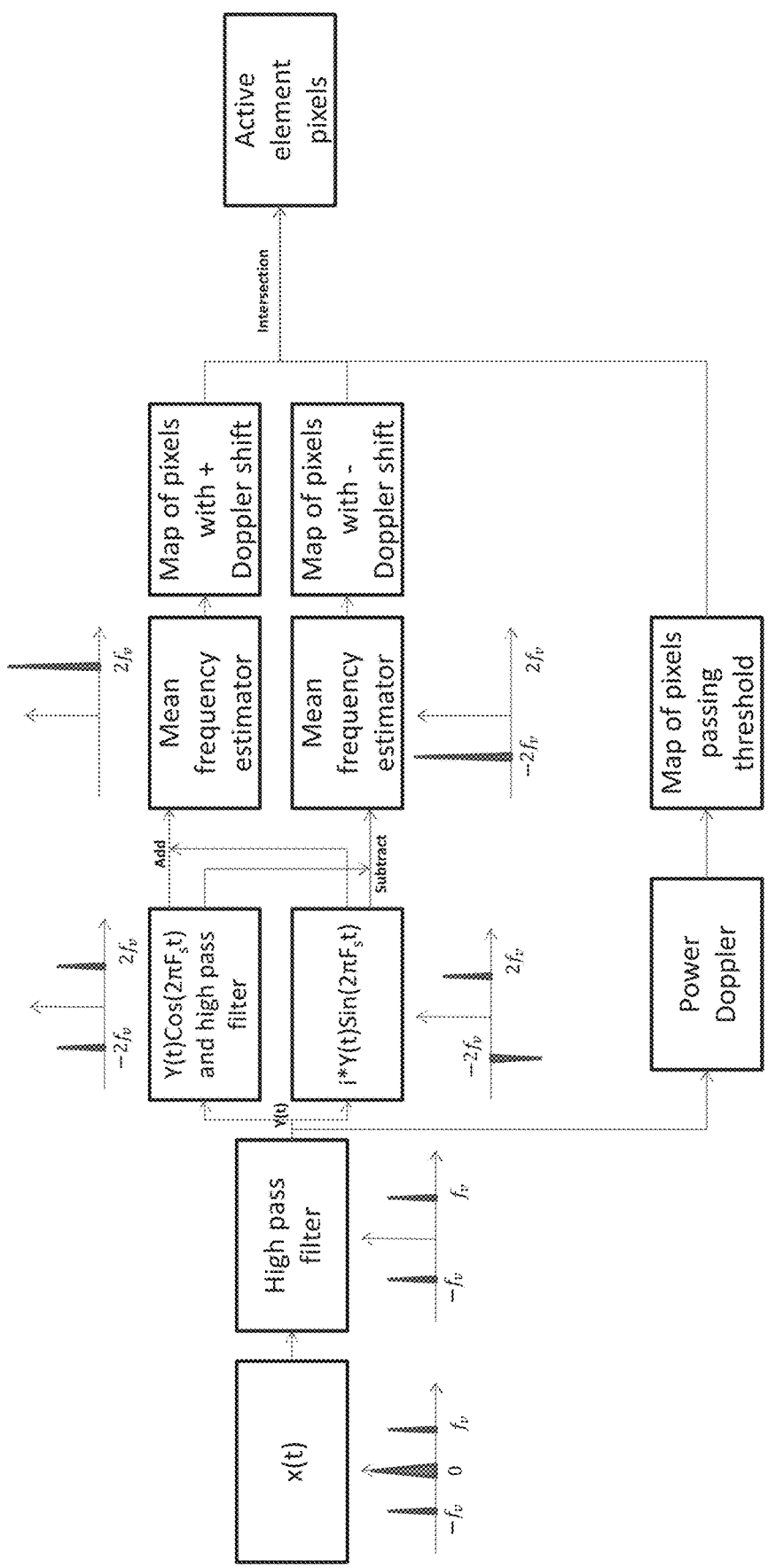
FIG. 2 is a flowchart setting forth the steps of an example method for localizing and/or tracking a medical device based on symmetric Doppler shifts measured with an ultrasound imaging system using a time domain approach.

Described here are systems and method for using ultrasound to localize a medical device (e.g., a catheter, implantable medical device, surgical implant) to which an active ultrasound element that can transmits ultrasound energy is attached. Doppler images of the medical device are acquired while the active element is transmitting ultrasound energy, and the images are processed to detect symmetric Doppler shifts associated with the active element. Because the systems and methods described in the present disclosure detect symmetric Doppler shifts to identify spatial points associated with the active element and, therefore, can be referred to as a symmetric frequency detection ("SFD") technique. The systems and methods described in the present disclosure enable tracking and display of one or more locations on or associated with the medical device. Thus, in some instances the tip of a catheter can be tracked or otherwise localized. In some other instances, the position and orientation of a surgical implant or implantable medical device can be tracked, localized, or otherwise monitored.

In some implementations, the systems and methods described in the present disclosure can identify these symmetric Doppler shifts and visualize them with a unique color. The signal strength of the active element can be varied to choose between finer localization and a quicker, coarse localization. This enables two different modes of operation enabling quicker localization or more precise positioning. The relative position of active element with respect to the imaging device can also be determined and provided to a user in both two and three dimensions. The active element can also be arranged to define a plane to help in guiding the medical device to the desired plane.

The systems and methods described in the present disclosure provide a number of additional advantages and benefits. As one example, the systems and methods described in the present disclosure do not interfere with Color Doppler imaging. As another example, multiple active elements can be tracked and displayed with unique colors. Different techniques for tacking multiple different active elements are also described. The systems and methods described in the present disclosure also enable localization or tracking of a medical device both in tissue and flow regions, and can enable visualization in a plane perpendicular to the medical device. In addition, precise localization of the active elements can be achieved with an accuracy of a few millimeters. The systems and methods described in the present disclosure are also compatible with existing ultrasound imaging systems with minimal, if any, changes to hardware, and can be used with both B-mode and Doppler imaging modes.

In some examples, the medical device can include a catheter with an acoustically active tip. In such devices, a miniature piezoelectric crystal is coupled to the tip of the catheter to act as a "beacon" that allows unique and accurate localization of the catheter tip by pulsed-wave (PW) Doppler imaging. The PW Doppler navigation method can localize the catheter tip within a few millimeters of a point target. Using an active acoustic point source on the tip of the catheter provides a smaller target that allows for better localization of the source of vibration.

In other examples, the medical device can include a surgical implant or an implantable medical device. In such devices, one or more active elements can be used to track, localize, or otherwise monitor the position and orientation of one or more portions or components of the device.

In still other examples, the medical device can include a device used in minimally invasive or other surgical procedures. Such devices may include a transcutaneous needle, a steerable sheath catheter, a catheter used for various investigative or therapeutic purposes, a biopsy device, a micromanipulator, an endoscope, and so on. In such devices, one or more active elements can be used to track, localize, or otherwise monitor the position and orientation of one or more portion or components of the device.

The systems and methods described in the present disclosure provide tracking of such medical devices by detecting symmetric Doppler shifts produced by interactions of the vibrating piezoelectric crystal in the active element and the incident ultrasound signal from the ultrasound imaging system. As described, the active elements can be visualized using a distinct color scheme in a PW Doppler imaging setup.

An incident ultrasound pulse-echo wave with transmit frequency, $f_c$, scattered by a surface vibrating at a frequency, $F_s$, results in a scattered wave containing frequency components $f_c \pm nF_s$, where n is an integer. The change in the frequency component of the scattered wave is due to the Doppler shift and acoustic nonlinearities in the bulk of the fluid. The prevalence of one phenomenon over the other (e.g., Doppler versus nonlinearity) is determined by factors such as vibration amplitude, low frequency pressure, or distance between vibrating surface and receiving transducer. Irrespective of the phenomenon, both lead to spectral sidebands around the center frequency, $f_c \pm nF_s$. The transmit frequency may be the center frequency, or another suitable transmit frequency of an active element. Thus, while reference is made in some instances to the center frequency, it will be appreciated that the positive and negative Doppler shifts can be measured more generally relative to any other suitable frequency value, including the transmit frequency of a particular active element.

The effect of bulk nonlinearities are negligible compared to the Doppler shift when the scattering happens in water or soft tissue, as opposed to air. In water, the Doppler effect is more dominant at higher frequencies (e.g., $f_c$ in MHz range), whereas in air it is more dominant at lower frequencies. The effect of bulk nonlinearities increases as the distance between vibrating surface and receiving transducer increases, but is negligible close to the vibrating surface. In addition, $F_s$ is fairly low (e.g., a few kHz) compared to $f_c$ (e.g., a few MHz), and its wavelength is long compared to the typical distance between the ultrasound imaging probe and the medical device. Based on the above considerations, the Doppler shift dominates bulk nonlinearity effects for the conditions common to the applications described in the present disclosure. The spectral sidebands can be referred to as the Doppler shift.

The Doppler shift in the incident wave with frequency $f_c$ due to modulation by a vibrating surface with frequency, $F_s$, can be described as follows. As noted, the nonlinear bulk effects can be ignored. The instantaneous angular frequency, $\omega_i(t)$, of a wave reflected from a vibrating surface can be approximated as, $$\omega_i(t) = \omega_c + \Delta\omega \cos(\omega_s t) \qquad (1);$$

where $\omega_c = 2\pi f_c$, is the center angular frequency, $\omega_s = 2\pi F_s$ is the frequency of the vibrating surface, and $\Delta\omega$ is the peak frequency deviation value. Because the instantaneous phase $\theta(t)$ is the time integral of the instantaneous angular frequency, $$\theta(t) = \omega_c t + \left(\frac{\Delta\omega}{\omega_s}\right)\sin(\omega_s t). \qquad (2)$$

Defining the modulation index $b=\Delta\omega/\omega_c$, Eqn. (2) can be rewritten as, $$\theta(t)=\omega_c t+b\sin(\omega_s t) \qquad (3).$$

The equation of the reflected wave can be rewritten in complex form as, $$\begin{aligned} y(t) &= \text{Re}\{Ae^{j\theta(t)}\} \\ &= \text{Re}\{Ae^{j(\omega_c t+b\sin(\omega_s t))}\}; \\ &= \text{Re}\{Ae^{j\omega_c t}e^{jb\sin(\omega_s t)}\} \end{aligned} \qquad (4)$$

where A is the amplitude of the ultrasound signal and Re{ } denotes the real part of the complex quantity. Eqn. (4) can be rewritten as, $$y(t)=\text{Re}\left\{A\sum_{n=-\infty}^{\infty}J_n(b)e^{j(\omega_c+n\omega_s)t}\right\}; \qquad (5)$$

where $J_n(b)$ is the nth order Bessel function of the first kind. The frequency spectrum of y(t) can be obtained by taking the Fourier transform of this signal. Hence, the Fourier transform of Eqn. (5) can be given as, $$Y(\omega)=A\pi\sum_{n=-\infty}^{\infty}J_n(b)[\delta(\omega-(\omega_c-n\omega_s))+\delta(\omega+(\omega_c+n\omega_s))]; \qquad (6)$$

where $\delta(\cdot)$ is the Dirac delta function. Thus, the frequency spectrum $Y(\omega)$ has peaks at angular frequencies $\omega_c\pm n\omega_s$, where n is an integer. Since $\omega_c=2\pi f_c$, the peaks will be found at frequencies $f_c\pm nF_s$.

Referring now to FIG. 1, a flowchart is illustrated as setting forth the steps of an example method for localizing one or more active elements that are coupled to a medical device and generating a display that identifies the location of the one or more active elements based on Doppler ultrasound. The method includes providing Doppler signal data, which may include signals or images, to a computer system, as generally indicated by process block 102. In general, the Doppler signal data form an ensemble of a number of different time frames. Providing these Doppler signal data can include retrieving previously acquired data from a memory or other suitable data storage, or may include acquiring such data with an ultrasound system. In either case, the Doppler signal data are acquired from a volume (e.g., a volume in a subject) containing a medical device having coupled thereto one or more active elements operating at one or more vibration frequencies, $F_s$, to acoustic energy (e.g., ultrasound energy or other acoustic energy) at the one or more vibration frequencies.

The Doppler images can be pre-processed. As one non-limiting example, the Doppler images can be pre-processed using a high-pass filter, which may be initialized using an initializing technique. For instance, a projection initialization clutter filter can be used to high-pass filter (e.g., with a cut-off frequency of 100 Hz) the signal to remove unwanted harmonics that could potentially result in aliasing and to remove low frequency signals from tissue movement.

When acquiring Doppler signal data, in order to detect a signal from the vibrating piezoelectric crystal of the one or more active elements using an ultrasound scanner, the vibration frequency, $F_s$, of the one or more active elements can in some implementations be chosen such that at least one pair of the resulting Doppler components falls within the Doppler bandwidth of the ultrasound scanner. Values of vibration frequency, $F_s$, higher than the Doppler bandwidth may result in aliasing of the frequency. Higher values of $F_s$ will lower the voltage applied to the active element and increase the acoustic output of the active element, as the resonance frequency of the active element is generally in the megahertz range (e.g., 1.2 MHz).

Lower voltages result in lower acoustic output and, therefore, may offer a safer mode of operation. However, aliased signals from multiple active elements can interfere with each other; thus, in these instances the aliasing frequency should be selected such that if aliasing of the two active signals occurs then the aliased signals destructively interfere with each other.

The one or more active elements may be excited by a variety of signals, including sinusoidal signals, non-sinusoidal signals, and coded signals. Coded signals allow for fitting more active elements in the limited Doppler bandwidth.

The Doppler frequency shift, $F_d$, in the signal reflected from a source moving at a velocity, v, can be calculated as, $$F_d=\frac{2f_c v\cos(\phi)}{c}; \qquad (7)$$

where $f_c$ is the ultrasound transmit frequency, $\phi$ is the incident angle, and C is the ultrasound speed in the medium, which is approximately 1,480 m/s for water and 1,540 m/s for most tissues.

Clinical ultrasound scanners are designed to show flow velocity within a certain range. Assuming that the maximum velocity that an ultrasound system can show is $v_{max}$, then, the maximum Doppler frequency shift, $F_{d,max}$ is, $$F_{d,max}=\frac{2f_c v_{max}\cos(\phi)}{c}. \qquad (8)$$

By choosing $F_s$ such that $nF_s<F_{d,max}$, the acquired Doppler images can be used to observe at least 2n Doppler components (both positive and negative Doppler shifts) of the crystal in the ultrasound catheter tip.

As one non-limiting example, to use an active element frequency of 3 kHz to visualize both the positive and negative Doppler shift, a maximum frequency of 4 kHz can be sufficient and implies a Nyquist criterion of 8 kHz for the sampling frequency.

The frequency resolution can be given as, $$\Delta f=\frac{PRF}{el'}; \qquad (9)$$

where el' is the modified ensemble length rounded up to the next power of two, and PRF is the pulse repetition frequency of the ultrasound probe. In order to have a frequency component at the active element excitation frequency, the active element can in some implementations be excited at frequencies given by, $$f_{cath}=\left(\frac{el'}{2}-N\right)\cdot\Delta f; N\in Z^+, \frac{el'}{2}>N>1. \qquad (10)$$

Referring still to FIG. 1, spectral data are generated by computing a Fourier transform of the Doppler image ensemble, as indicated at step 104. The Fourier transform can be implemented, for instance, using a fast Fourier transform ("FFT") of the Doppler signal taken through each point in space. To make the FFT more efficient, an ensemble length of the Doppler images can be selected such that the sample length is a multiple of two. As one example, the ensemble length can be selected as 32.

In general, spatial points representing the one or more active elements will have a Doppler shift in the neighborhood of the active element frequency. Because the signal from the active elements may be weak compared to the signal from the neighboring tissue, the signal and noise strength around the one or more active element frequencies is estimated.

The signal strength at the active element frequency is calculated, as indicated at step 106. As one example, the signal strength at the active element frequency can be estimated using a window function centered at a frequency of the active element. The window function may be a Gaussian window, as one example. The Gaussian window can be centered at a frequency of the catheter tip, and a standard deviation of a prescribed amount of the active element frequency can be used to extract the signal around the active element frequency. As one example, the standard deviation can be 5 percent.

The noise strength is also calculated, as indicated at step 108. As one example, the noise strength can be estimated using one or more window functions positioned about frequencies other than the active element frequency. In general, the one or more window functions used to estimate the noise strength will be different from the window function used to estimate the signal strength. As an example, two rectangular windows can be used to estimate the noise strength from other frequencies around the active element frequency, but excluded those frequencies spanned by the window used to estimate the signal strength.

A threshold parameter, $\alpha$, is computed using the signal strength and the noise strength. For instance, the threshold parameter can be computed as the ratio of the signal power at the active element frequency to the noise power in the neighborhood of the active element frequency. This process is optionally repeated, as indicated at decision block 110, if there are additional active elements operating at different vibration frequencies. If so, the signal strength and noise strength at these frequencies is then estimated, and a threshold parameter associated with that frequency is computed.

The Doppler images are then processed at process block 112 using the computed threshold parameter, or parameters when multiple active elements are used, to identify those spatial points that are potentially associated with the one or more active elements. For example, all spatial points satisfying the threshold requirement and being located within the frequency range of the one or more active elements are identified as potentially associated with an active element and are passed through an adjacency filter, as indicated at step 114. In general, the adjacency filter, or another suitable filter, is used to remove all connected components that had less than a prescribed number of pixels, which may be, for example, six pixels. The centroid of the remaining pixels is then computed, as indicated at step 116. The centroid can be computed and displayed as an ellipse, as one example.

The above-mentioned process can be applied to all points in both the positive and negative Doppler shift frequencies. For instance, steps 106-116 can be performed once using an active element frequency set as the positive Doppler shift frequency and one using an active element frequency set as the negative Doppler shift frequency.

All spatial points satisfying the signal-to-noise threshold criteria for both positive and negative shift and the adjacency filter are classified as the catheter tip. As indicated at step 118, the identified pixels can be used to generate a display that depicts a localization of the one or more active elements, which provides a localization of the medical device to which the one or more active elements are coupled. As one example, the display is an image that is generated by overlaying the identified pixels on B-mode or Doppler images. In some instances, the identified pixels can be overlaid on B-mode or Doppler images after passing through a Gaussian smoothing filter. As one example, the Gaussian smoothing filter can have a standard deviation of 0.6 and a kernel of size 0.62 mm in the axial direction and 0.60 mm in the lateral direction.

As another example, the generated display can include a binary color map that is generated by assigning binary colors to the identified pixels. This binary color map can be overlaid on B-mode or Doppler images. The binary color map can use a color (e.g., yellow) that is distinct from the conventional colors used in Doppler images (e.g., the red-blue Doppler color) to provide a unique visualization of the one or more active elements. When the medical device includes multiple active elements, the generated display can track and display the multiple active elements with unique colors. For instance, a different color can be assigned to different active elements. In such instances, the binary color map may instead be a color map containing more than binary color values (e.g., two or more colors instead of one color).

In still other examples, in addition to visualizing the one or more active elements, the generated display can include information about the distance within which an active element can be spatially localized. Localization distance can be defined as the spot size that the piezoelectric crystal of an active element occupies in B-mode when vibrating. A short localization distance implies more accurate spatial tracking of the catheter tip. The localization distance depends on the scanning transducer and the piezoelectric crystal of the active element.

In general, the piezoelectric crystal in the active element may be spherical in shape and omnidirectional in signal transmission. The localization distance in the azimuthal scanning direction will typically depend on the ultrasound beam width and the crystal size. However, in the axial direction, the localization accuracy will depend on the axial resolution of the linear array transducer and the crystal size. The axial resolution is usually submillimeter for both conventional and plane wave B-mode images. In the axial direction, the signal-to-noise ratio depends on the axial depth.

When the signal strength from both components of a given active element is greater than the threshold, a, the systems and methods described in the present disclosure can identify the active element. Elevational direction is a relevant consideration for localizing an active element. The localization distance in elevational direction can depend on the ultrasound slice thickness (ST) and the size of the piezoelectric crystal (Dc). The elevational direction can also depend on the noise and dynamic range. When the piezoelectric crystal is within the ST of the ultrasound imaging plane, Doppler shifts are generated and thus can be detected by the Doppler system. However, if the crystal moves away from the beam, the amplitude of the ultrasound signal reflected by the crystal decays and the Doppler shifts due to the crystal may no longer be detectable. Therefore, the localization distance in the elevational direction can be defined as, $$L_e = \frac{ST}{2} + D_e; \qquad (11)$$

Figure 5:
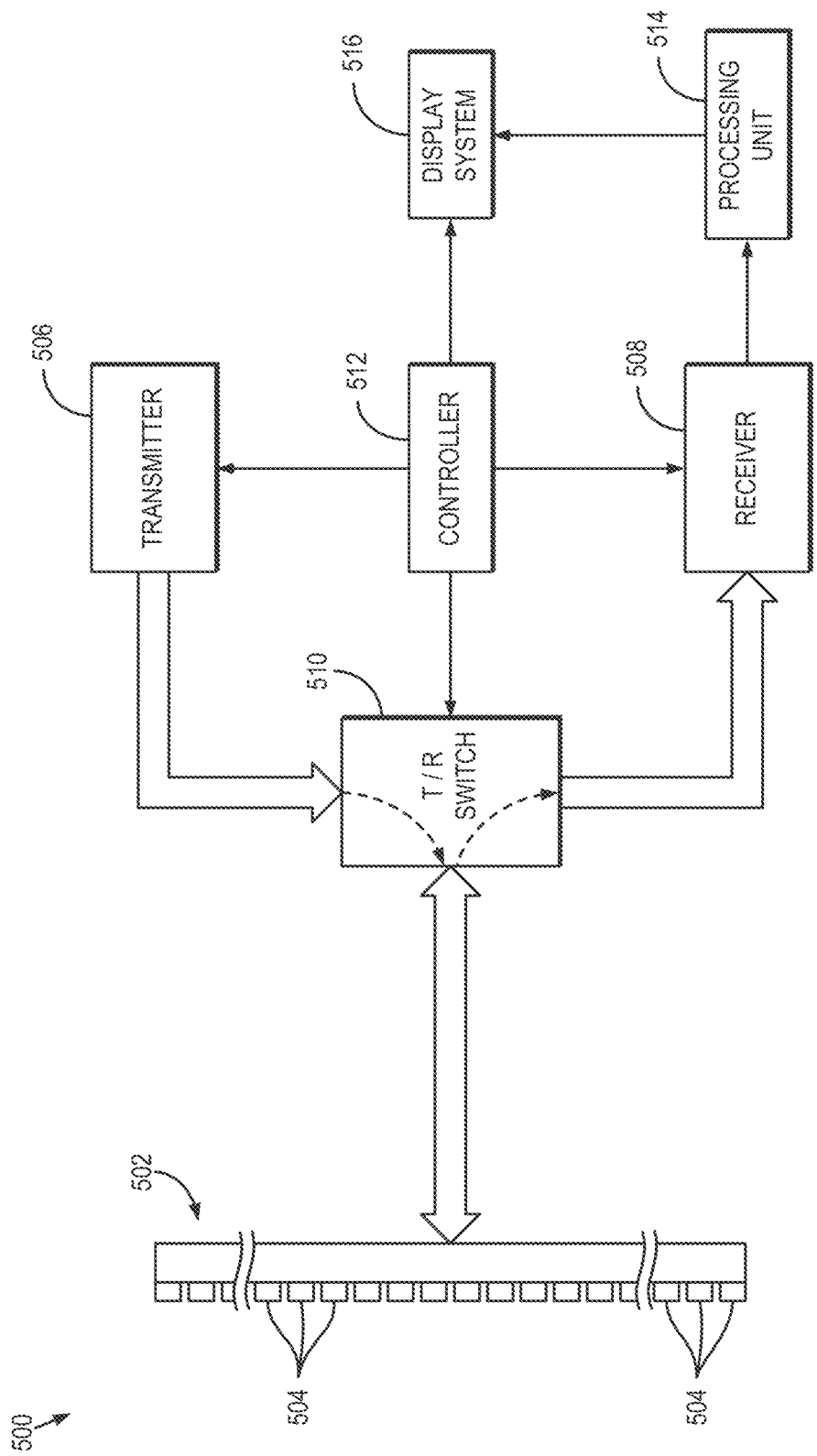
FIG. 5 is a block diagram of an example ultrasound imaging system that can be implemented to acquired Doppler images.

In addition to using a frequency domain analysis, the spatial pixels representing the active elements can be identified in the time domain (e.g., by analyzing the temporal evolution of signals in the ensemble of Doppler images, rather than the spectral data generated by Fourier transforming the ensemble into the frequency domain), as shown in FIG. 5. In some instances the time domain signal can be high-pass filtered to remove low-frequency tissue motion.

The time domain signal is modulated with one or more functions by the active element excitation frequency, $F_s$, which may include a sine and cosine. For instance, the time domain symmetric Doppler shift signal, X(t), can be expressed as, $$X(t) = A_1 e^{j\omega t} + A_2 e^{-j\omega t} \qquad (12);$$

where $A_1$ and $A_2$ are the amplitude of the positive and negative Doppler shift, and $\omega = 2\pi F_s$ is the frequency of the Doppler shift due to the vibration frequency. After high-pass filtering, the signal, Y(t), can be written as, $$Y(t) = X(t) \cdot h \qquad (13);$$

where h is the impulse response of a high-pass filter. The signal, Y(t), can be modulated by a cosine function of the same frequency as the active element. The resultant modulated signal, $Y_1(t)$, can be expressed as, $$Y_1(t) = Y(t) \cdot \left( \frac{e^{j\omega t}}{2} + \frac{e^{-j\omega t}}{2} \right) \qquad (14)$$
$$= \frac{A_1 e^{j2\omega t}}{2} + \frac{A_1}{2} + \frac{A_2}{2} + \frac{A_2 e^{-j2\omega t}}{2}.$$

Similarly, after modulating the signal, Y(t), with a sine function of the same frequency as the vibration frequency the resultant modulated signal, $Y_2(t)$, can be expressed as, $$Y_2(t) = Y(t) \cdot \left( \frac{e^{j\omega t}}{2} - \frac{e^{-j\omega t}}{2} \right) \qquad (15)$$
$$= \frac{A_1 e^{j2\omega t}}{2} + \frac{A_1}{2} + \frac{A_2}{2} - \frac{A_2 e^{-j2\omega t}}{2}.$$

Summing or subtracting results in the cancellation of the other symmetric component. The summation of the two modulated signals, $Z_1(t)$, can be expressed as, $$Z_1(t) = Y_1(t) + Y_2(t) = A_1 e^{j2\omega t} + A_1 + A_2 \qquad (16).$$

The difference of the two modulated signals, $Z_2(t)$, can be expressed as, $$Z_2(t) = Y_1(t) - Y_2(t) = A_2 e^{-j2\omega t} \qquad (17).$$

The summation signal, $Z_1(t)$, represents the isolated positive Doppler shift and the difference signal, $Z_2(t)$, represents the isolated negative Doppler shift.

With positive and negative Doppler shifts isolated, mean frequency estimators (e.g., Kay estimators) can be used to identify the location of the spatial pixels showing positive and negative Doppler shifts (e.g., at a frequency of 2ω). As noted above, if the frequency, ω, is greater than the Doppler bandwidth then the signal will appear with the Doppler bandwidth after aliasing. In some instances, the mean frequency estimators can output spatial maps depicting the spatial distribution of the positive Doppler shifts and negative Doppler shifts. The strength of the signal having both positive and negative Doppler shifts can also be assessed based on a power Doppler map generated from the Doppler images, or the high-pass filtered Doppler images. The intersection of the positive and negative Doppler shift maps can identify the points having both positive and negative Doppler shifts, thereby identifying the location of the one or more active elements. Additionally or alternatively, the intersection of the positive Doppler shift pixels, negative Doppler shift pixels, and the power Doppler can also help identify the active element pixels.

As noted above, in some implementations multiple different active elements can be tracked. In these instances, multiplexing techniques can be used to facilitate the localization and tracking of these multiple active elements. For instance, in general methods for multiplexing excitations to multiple active elements, such that each can be uniquely detected (e.g., by demodulating the Doppler signal in the ultrasound system) and its location displayed as desired.

As one example, a frequency division multiplexing ("FDM") method using a multiple signal classification ("MUSIC") algorithm can be used to track multiple active elements. In some particular implementations, a super-resolution MUSIC algorithm can be used. In this approach, active elements transmit signals (e.g., sinusoidal signals) at different frequencies. Generally, super-resolution frequency estimation is often required for multicomponent sinusoidal signals, which is able to separate signals spaced more closely than the resolution limit in the frequency domain. As noted above, a MUSIC algorithm can be used for frequency estimation, while enabling higher resolution than methods based on a discrete Fourier transform ("DFT").

In general, implementing a MUSIC algorithm assumes that the received signal contains 2N complex exponential signals (equivalent to N sinusoid waves) in the presence of Gaussian white noise. A P×P covariance matrix (where P is the number of samples) is computed. The eigenvalues of the covariance matrix are then stored in decreasing order. The eigenvectors corresponding to the 2N largest eigenvalues span the signal subspace and can be selected or otherwise stored as the relevant signal information from which the active elements can be tracked or otherwise located. The remaining 2P-M eigenvectors span the orthogonal space where there is only noise. MUSIC outperforms simple methods, such as picking the peaks of DFT spectra in the presence of noise. Unlike DFT, MUSIC can estimate frequencies with accuracy higher than one sample (i.e., super-resolution), because its estimation function can be evaluated for any frequency, not just those of DFT bins.

The MUSIC algorithm can assume that coexistent sources are uncorrelated. Recent iterative semi-parametric methods (e.g., iterative sparse asymptotic minimum variance ("SAMV")) offer robust super-resolution despite highly correlated sources. Although the computational complexity of MUSIC is higher than that of a DFT-based periodogram, since each data set contains a smaller number of samples, the computational time for the small covariance matrix in MUSIC can be very short, thus allowing real-time detection of multiple signals.

As another example, time division multiplexing ("TDM") can be implemented for tracking multiple active elements, which can be used to overcome or otherwise address the challenge of fitting more active elements into the limited Doppler bandwidth. Time multiplexing is a technique that can be used to display active elements at different times. In the TDM implementation, active elements are activated in two or more temporally distinct groups. For instance, active elements can be activated in two groups in alternating sequential time slots. That is, active elements 1 and 2 are active for one ultrasound transmit and processing events, and active elements 3 and 4 are active for the subsequent ultrasound transmit and processing events. To identify each active elements uniquely, active elements 1 and 2 can be excited at 2 kHz and 3 kHz, respectively, whereas active elements 3 and 4 can be excited at 2.5 kHz and 3.5 kHz, respectively. Thus, in general, the active elements are excited at different frequencies so that the algorithm can distinctly display the active elements (e.g., in distinct marker colors or with distinct marker shapes, such as circles, squares, stars, and so on) for easy identification by the user. The time slots can be repeated with a frequency (e.g., every 61.5 ms) sufficient so the display elements or markers representing the active elements (e.g., color spots) can be displayed to appear without blinking.

To accommodate more active elements, the processing time can be reduced with a trade-off that separating an increasing number of different frequencies will be more challenging. The reduction in processing time can be achieved by optimizing the processing (e.g., by using more efficient codes or using parallel processing to minimize the time), by utilizing faster hardware (e.g., hardware with a higher number of cores and more memory to speed up the processing), or combinations thereof. In addition to being implemented with plane-wave ultrasound systems, the TDM algorithm can also be implemented in traditional "scan line based" ultrasound systems, albeit with a potentially lower frame rate as compared to using plane-wave imaging.

Reducing the processing time can enable a higher frame rate and more active elements. In general, the time frame per active element can be calculated using the following equation:

$$\frac{\text{frame rate}}{\text{active element}}(\text{Hz}) = \frac{1000}{\left((T_p + T_{acq} + T_{switching})\frac{n_c}{2}\right)}; \quad (18)$$

where $T_p$ is the processing time in ms, $T_{acq}$ is the acquisition time in ms, $T_{switching}$ is the switching time from one active element to another in ms, and $n_c$ is the number of active elements (e.g., crystals). Overall, TDM is technologically simple to implement, but may be limited in the number of active elements that can be identified distinctively.

As still another example, code division multiplexing ("CDM") can be implemented to track or otherwise locate multiple active elements. This approach is based on code division multiplexing of the transmitted signal by different active elements. In the CDM strategy, pseudo-orthogonal spreading sequences can be used to separate signals from multiple active elements (e.g., piezoelectric crystals). A spreading sequence is a sequence of N bi-polar +1 and −1 bits (or chips) arranged in random order. This signal has a wide bandwidth, and ideally covers the entire allowable bandwidth (e.g., 4 kHz). Each sequence called the "spreading signal," has a unique pattern of ±1's that is assigned to each source (i.e., an active element). In a set of pseudo-orthogonal sequences, the pattern of ±1 bits are chosen such that the cross-correlation of each pair of the set is either 1 or −1; however, the autocorrelation of a sequence with itself is N. Therefore, by correlating a particular sequence to the received signal, it is possible to detect the coded sequence with the matching pattern. That is, each sequence acts as the key for decoding (i.e., detecting) the source transmitting the same sequence. The process of detection in this context is called "de-spreading." One advantage of spreading and de-spreading is that it improves the signal power and makes it possible to transmit multiple distinct signals over the same bandwidth.

In this approach, active elements sources transmit using different "spreading sequences" (i.e., coded signals). As one non-limiting example, "maximum length sequence" (m-sequence, or MLS) can be used as the spreading sequence. After de-spreading using matched filtering, active element source, k, is amplified equally to processing gain. The cross terms with the desired spreading sequence and other spreading sequences generate interference. Therefore, the cross-correlation coefficients of the m-sequence are determined. The circular autocorrelation of an m-sequence (MLS) is a Kronecker delta function. Considering a code sequence composed of ±1, the normalized autocorrelation term is equal to 1 and cross-correlation term is equal to (−1)/N, where N is the code length.

The number of supportable active elements sources using CDM without blood flow (i.e., non-vascular applications) can be estimated as follows. In some clinical applications of minimally invasive devices, such as guiding biopsy needles, there is no significant blood flow near the device. In such applications, it can be possible to ignore the noise from blood flow. To estimate the number of supportable active elements using CDM in such situations, the maximum processing gain of a spreading sequence, which directly depends one the bandwidth ratio of the signal before and after de-spreading, is estimated. To estimate the bandwidth of signal before spreading, the frequency resolution is estimated. Frequency resolution can be determined as, $F_s/N_s$, where $N_s$ is a number of data points in the ensemble. As one non-limiting example, the ensemble length can be $N_s$=32 and $F_s$=Doppler PRF=8 KHz; as a result, the frequency resolution in this example is $F_s/N_s$=250 Hz. The processing gain for the maximum code length is, $$PG = 10\log_{10}\left(BW\frac{F_s}{N_s}\right). \quad (19)$$

Therefore, for a bandwidth of BW=4 KHz and $F_s$=8 KHz and $N_s$=32, the processing gain will be PG=12 dB.

In the CDM technique described above, the length of the spreading sequence (N) is equal to the progressing gain in linear scale, $$N = 10^{(PG/10)} - 1 \quad (20).$$

In the non-limiting example described above (i.e., for PG=12 dB, BW=4 KHz, $F_s$=8 KHz, $N_s$=32) the spreading sequence length is N=15. When the m-sequence is used as the spreading sequence, cross-correlation between different m-sequences is −1/N. This non-zero cross-correlation acts as interference noise. Hence, using multiple active element sources, $N_c$, the SNR due to the interference is, $$SNR = 10\log_{10}\left(\frac{N}{N_c}\right). \quad (21)$$

Therefore, depending on the acceptable SNR for detection of the active element signal, the number of potentially detectable active elements, $N_c$, can be determined. For example, assuming N=15, the SNR will be 8.8 dB for $N_c$=2, 7 dB for $N_c$=3, 5.74 dB for $N_c$=4, and 2.21 dB for $N_c$=9. Hence, if a minimum SNR of 1-2 dB is acceptable for detection, the number of supportable active element sources can be $N_c$=9. Another way to determine the number of supportable crystals $N_c$ is in terms of probability of error.

When the device to be guided is used in blood vessels or the heart, such as intracardiac catheters, the Doppler signal from blood flow act as the major source of noise in acoustically detecting the active elements. In general, the number of supportable crystals will depend on the noise (i.e., mainly from blood flow), interference from the signals of other active elements, and the acceptable detection error. Therefore, the number of supportable active elements can be estimated versus the SNR for a given rate of acceptable detection error. The noise can be defined as the noise from blood flow or the inherent system noise (excluding the interference due to signals from other active elements).

Figure 3:
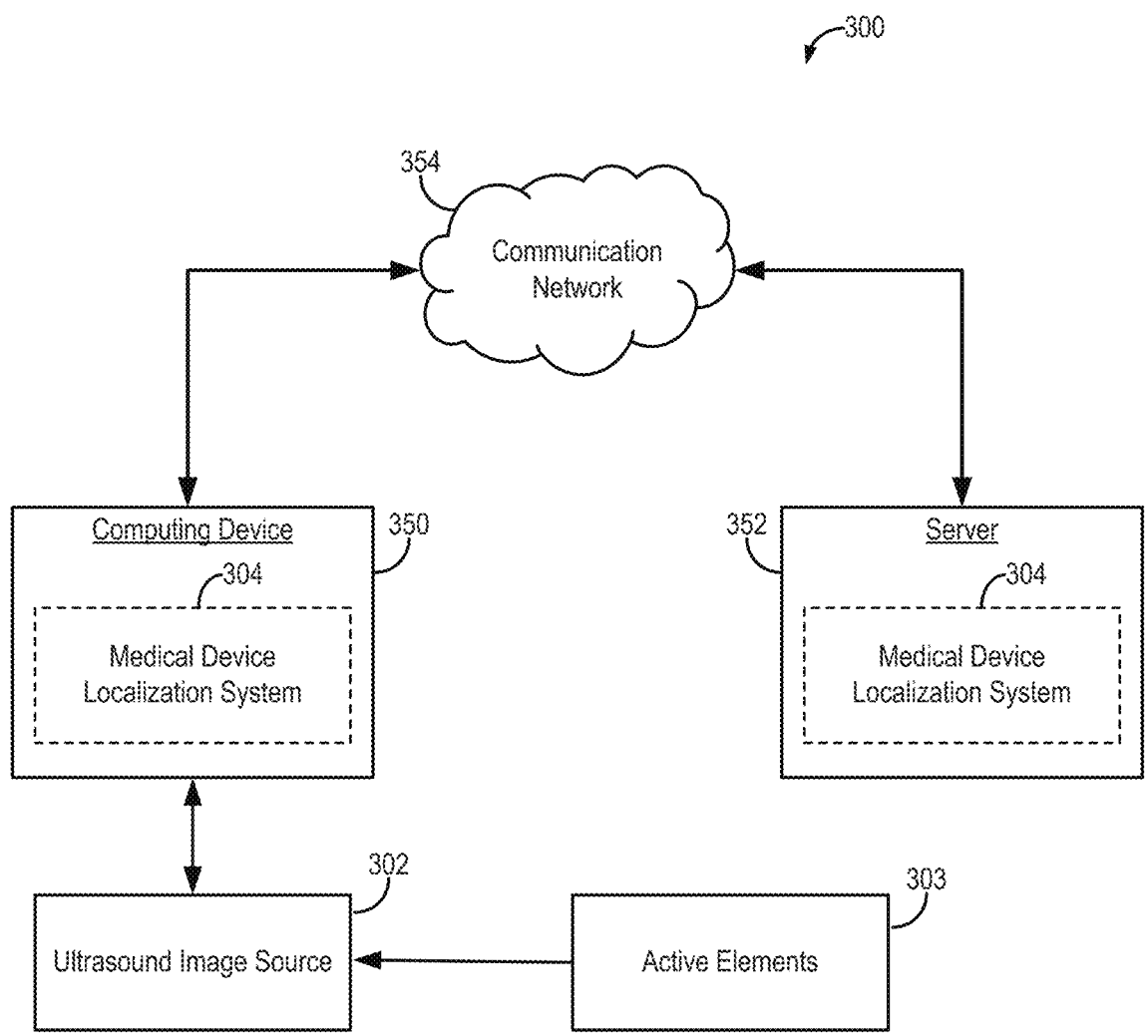
FIG. 3 is a block diagram of an example system that can implement the methods described in the present disclosure.

Referring now to FIG. 3, an example of a system 300 for tracking or otherwise visualizing a medical device (e.g., a catheter, a surgical implant, an implantable medical device) in accordance with some embodiments of the systems and methods described in the present disclosure is shown. As shown in FIG. 3, a computing device 350 can receive one or more types of ultrasound data from ultrasound image source 302. In some embodiments, computing device 350 can execute at least a portion of a medical device localization system 304 to localize and/or track one or more active elements coupled to one or more locations of the medical device from ultrasound data received from the ultrasound image source 302.

Additionally or alternatively, in some embodiments, the computing device 350 can communicate information about ultrasound data received from the ultrasound image source 302 to a server 352 over a communication network 354, which can execute at least a portion of the medical device localization system 304 to localize and/or track the medical device from ultrasound data received from the ultrasound image source 302. In such embodiments, the server 352 can return information to the computing device 350 (and/or any other suitable computing device) indicative of an output of the medical device localization system 304 to localize and/or track a medical device from ultrasound data received from the ultrasound image source 302.

In some embodiments, computing device 350 and/or server 352 can be any suitable computing device or combination of devices, such as a desktop computer, a laptop computer, a smartphone, a tablet computer, a wearable computer, a server computer, a virtual machine being executed by a physical computing device, and so on. The computing device 350 and/or server 352 can also reconstruct images from ultrasound data.

In some embodiments, ultrasound image source 302 can be any suitable source of ultrasound image data, such as an ultrasound machine, another computing device (e.g., a server storing ultrasound image data), and so on. In some embodiments, ultrasound image source 302 can be local to computing device 350. For example, ultrasound image source 302 can be incorporated with computing device 350 (e.g., computing device 350 can be configured as part of a device for capturing, scanning, and/or storing ultrasound images). As another example, ultrasound image source 302 can be connected to computing device 350 by a cable, a direct wireless link, and so on. Additionally or alternatively, in some embodiments, ultrasound image source 302 can be located locally and/or remotely from computing device 350, and can communicate ultrasound data to computing device 350 (and/or server 352) via a communication network (e.g., communication network 354).

In some embodiments, communication network 354 can be any suitable communication network or combination of communication networks. For example, communication network 354 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, etc. In some embodiments, communication network 354 can be a local area network, a wide area network, a public network (e.g., the Internet), a private or semi-private network (e.g., a corporate or university intranet), any other suitable type of network, or any suitable combination of networks. Communications links shown in FIG. 3 can each be any suitable communications link or combination of communications links, such as wired links, fiber optic links, Wi-Fi links, Bluetooth links, cellular links, and so on.

Figure 4:
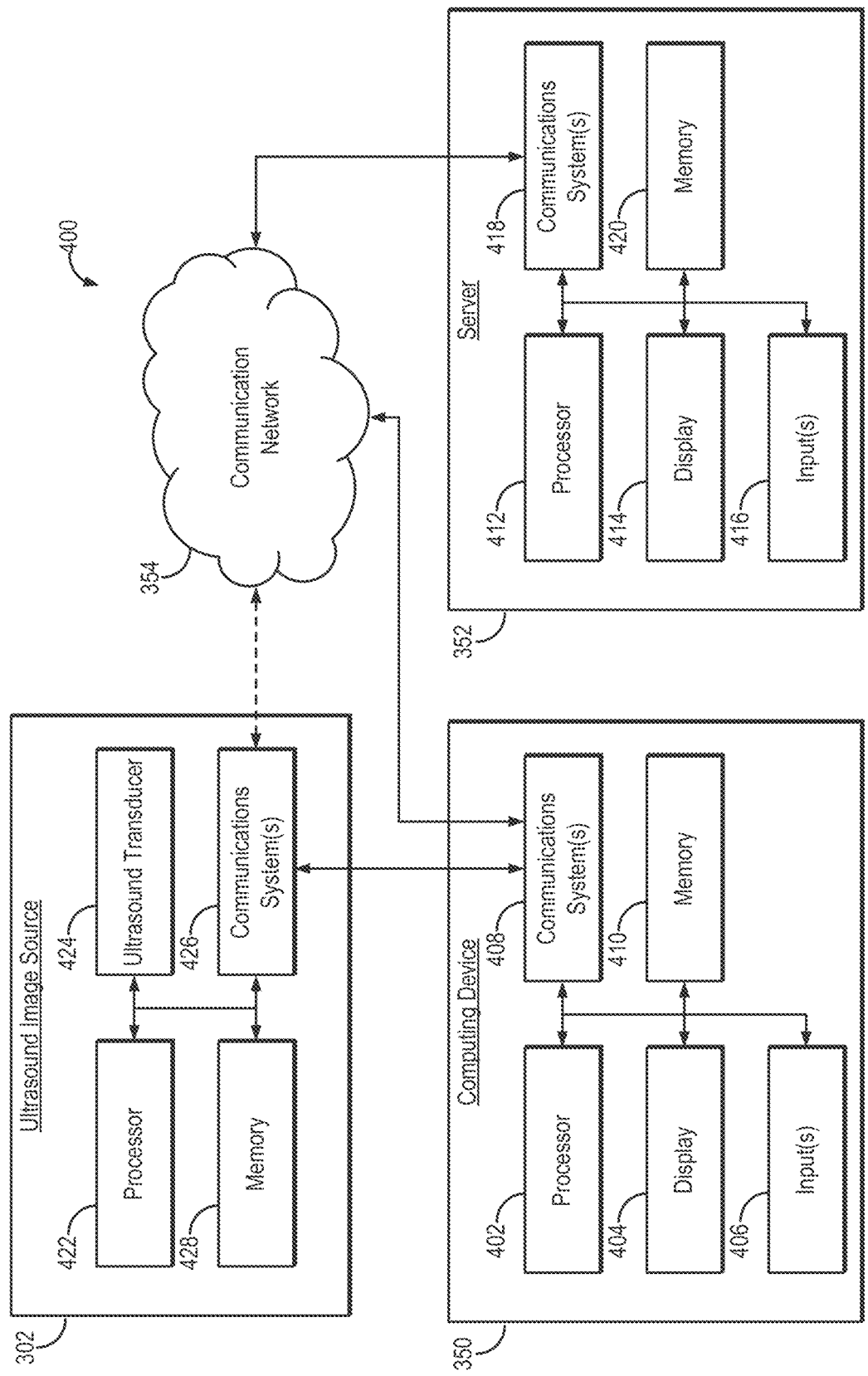
FIG. 4 is a block diagram of example hardware components that can be implemented in the system of FIG. 3.

Referring now to FIG. 4, an example of hardware 400 that can be used to implement ultrasound image source 302, computing device 350, and server 352 in accordance with some embodiments of the systems and methods described in the present disclosure is shown. As shown in FIG. 4, in some embodiments, computing device 350 can include a processor 402, a display 404, one or more inputs 406, one or more communication systems 408, and/or memory 410. In some embodiments, processor 402 can be any suitable hardware processor or combination of processors, such as a central processing unit ("CPU"), a graphics processing unit ("GPU"), and so on. In some embodiments, display 404 can include any suitable display devices, such as a computer monitor, a touchscreen, a television, and so on. In some embodiments, inputs 406 can include any suitable input devices and/or sensors that can be used to receive user input, such as a keyboard, a mouse, a touchscreen, a microphone, and so on.

In some embodiments, communications system(s) 408 can include any suitable hardware, firmware, and/or software for communicating information over communication network 354 and/or any other suitable communication networks. For example, communications system(s) 408 can include one or more transceivers, one or more communication chips and/or chip sets, and so on. In a more particular example, communications system(s) 408 can include hardware, firmware and/or software that can be used to establish a Wi-Fi connection, a Bluetooth connection, a cellular connection, an Ethernet connection, and so on.

In some embodiments, memory 410 can include any suitable storage device or devices that can be used to store instructions, values, etc., that can be used, for example, by processor 402 to present content using display 404, to communicate with server 352 via communications system(s) 408, etc. Memory 410 can include any suitable volatile memory, non-volatile memory, storage, or any suitable combination thereof. For example, memory 410 can include RAM, ROM, EEPROM, one or more flash drives, one or more hard disks, one or more solid state drives, one or more optical drives, etc. In some embodiments, memory 410 can have encoded thereon a computer program for controlling operation of computing device 350. In such embodiments, processor 402 can execute at least a portion of the computer program to present content (e.g., ultrasound images, user interfaces, graphics, tables, etc.), receive content from server 352, transmit information to server 352, etc.

In some embodiments, server 352 can include a processor 412, a display 414, one or more inputs 416, one or more communications systems 418, and/or memory 420. In some embodiments, processor 412 can be any suitable hardware processor or combination of processors, such as a CPU, a GPU, etc. In some embodiments, display 414 can include any suitable display devices, such as a computer monitor, a touchscreen, a television, etc. In some embodiments, inputs 416 can include any suitable input devices and/or sensors that can be used to receive user input, such as a keyboard, a mouse, a touchscreen, a microphone, etc.

In some embodiments, communications systems 418 can include any suitable hardware, firmware, and/or software for communicating information over communication network 354 and/or any other suitable communication networks. For example, communications systems 418 can include one or more transceivers, one or more communication chips and/or chip sets, etc. In a more particular example, communications systems 418 can include hardware, firmware and/or software that can be used to establish a Wi-Fi connection, a Bluetooth connection, a cellular connection, an Ethernet connection, etc.

In some embodiments, memory 420 can include any suitable storage device or devices that can be used to store instructions, values, etc., that can be used, for example, by processor 412 to present content using display 414, to communicate with one or more computing devices 350, etc. Memory 420 can include any suitable volatile memory, non-volatile memory, storage, or any suitable combination thereof. For example, memory 420 can include RAM, ROM, EEPROM, one or more flash drives, one or more hard disks, one or more solid state drives, one or more optical drives, etc. In some embodiments, memory 420 can have encoded thereon a server program for controlling operation of server 352. In such embodiments, processor 412 can execute at least a portion of the server program to transmit information and/or content (e.g., generated additional ultrasound data, ultrasound images, a user interface, etc.) to one or more computing devices 350, receive information and/or content from one or more computing devices 350, receive instructions from one or more devices (e.g., a personal computer, a laptop computer, a tablet computer, a smartphone, etc.), etc.

In some embodiments, ultrasound image source 302 can include a processor 422, an ultrasound transducer 424, one or more communications systems 426, and/or memory 428. In some embodiments, processor 422 can be any suitable hardware processor or combination of processors, such as a CPU, a GPU, etc. In some embodiments, ultrasound transducer 424 can be any suitable ultrasound probe configured to generate ultrasound data corresponding to one or more ultrasound imaging modes (e.g., B-mode ultrasound, color Doppler ultrasound, shear wave elastography ultrasound). Additionally or alternatively, in some embodiments, ultrasound transducer 424 can include any suitable hardware, firmware, and/or software for coupling to and/or controlling operations of an ultrasound transducer. In some embodiments, one or more portions of ultrasound transducer 424 can be removable and/or replaceable (e.g., with a transducer that is configured to generate ultrasound data corresponding to a different mode, that is configured to generate ultrasound data with higher or lower resolution, with a transducer that has a different sparse array characteristics, and so on).

Note that, although not shown, ultrasound image source 302 can include any suitable inputs and/or outputs. For example, ultrasound image source 302 can include input devices and/or sensors that can be used to receive user input, such as a keyboard, a mouse, a touchscreen, a microphone, a trackpad, a trackball, etc. As another example, ultrasound image source 302 can include any suitable display devices, such as a computer monitor, a touchscreen, a television, etc., one or more speakers, etc.

In some embodiments, communications systems 426 can include any suitable hardware, firmware, and/or software for communicating information to computing device 350 (and, in some embodiments, over communication network 354 and/or any other suitable communication networks). For example, communications systems 426 can include one or more transceivers, one or more communication chips and/or chip sets, etc. In a more particular example, communications systems 426 can include hardware, firmware and/or software that can be used to establish a wired connection using any suitable port and/or communication standard (e.g., VGA, DVI video, USB, RS-232, etc.), Wi-Fi connection, a Bluetooth connection, a cellular connection, an Ethernet connection, etc.

In some embodiments, memory 428 can include any suitable storage device or devices that can be used to store instructions, values, ultrasound data, etc., that can be used, for example, by processor 422 to control ultrasound transducer 424, and/or receive ultrasound data from ultrasound transducer 424; to generate ultrasound images from ultrasound data; present content (e.g., ultrasound images, a user interface, etc.) using a display; communicate with one or more computing devices 350; and so on. Memory 428 can include any suitable volatile memory, non-volatile memory, storage, or any suitable combination thereof. For example, memory 428 can include RAM, ROM, EEPROM, one or more flash drives, one or more hard disks, one or more solid state drives, one or more optical drives, etc. In some embodiments, memory 428 can have encoded thereon a program for controlling operation of ultrasound image source 302. In such embodiments, processor 422 can execute at least a portion of the program to generate ultrasound images, transmit information and/or content (e.g., ultrasound data) to one or more computing devices 350, receive information and/or content from one or more computing devices 350, receive instructions from one or more devices (e.g., a personal computer, a laptop computer, a tablet computer, a smartphone, etc.), etc.

FIG. 5 illustrates an example of an ultrasound system 500 that can implement the methods described in the present disclosure. The ultrasound system 500 includes a transducer array 502 that includes a plurality of separately driven transducer elements 504. The transducer array 502 can include any suitable ultrasound transducer array, including linear arrays, curved arrays, phased arrays, and so on. Similarly, the transducer array 502 can include a 1D transducer, a 1.5D transducer, a 1.75D transducer, a 2D transducer, a 3D transducer, and so on.

When energized by a transmitter 506, a given transducer element 504 produces a burst of ultrasonic energy. The ultrasonic energy reflected back to the transducer array 502 (e.g., an echo) from the object or subject under study is converted to an electrical signal (e.g., an echo signal) by each transducer element 504 and can be applied separately to a receiver 508 through a set of switches 510. The transmitter 506, receiver 508, and switches 510 are operated under the control of a controller 512, which may include one or more processors. As one example, the controller 512 can include a computer system.

The transmitter 506 can be programmed to transmit unfocused or focused ultrasound waves. In some configurations, the transmitter 506 can also be programmed to transmit diverged waves, spherical waves, cylindrical waves, plane waves, or combinations thereof. Furthermore, the transmitter 506 can be programmed to transmit spatially or temporally encoded pulses.

The receiver 508 can be programmed to implement a suitable detection sequence for the imaging task at hand. In some embodiments, the detection sequence can include one or more of line-by-line scanning, compounding plane wave imaging, synthetic aperture imaging, and compounding diverging beam imaging.

In some configurations, the transmitter 506 and the receiver 508 can be programmed to implement a high frame rate. For instance, a frame rate associated with an acquisition pulse repetition frequency ("PRF") of at least 100 Hz can be implemented. In some configurations, the ultrasound system 500 can sample and store at least one hundred ensembles of echo signals in the temporal direction.

The controller 512 can be programmed to implement a selected imaging sequence to acquire ultrasound data. In some embodiments, the controller 512 receives user inputs defining various factors used in the design of the imaging sequence.

A scan can be performed by setting the switches 510 to their transmit position, thereby directing the transmitter 506 to be turned on momentarily to energize transducer elements 504 during a single transmission event according to the selected imaging sequence. The switches 510 can then be set to their receive position and the subsequent echo signals produced by the transducer elements 504 in response to one or more detected echoes are measured and applied to the receiver 508. The separate echo signals from the transducer elements 504 can be combined in the receiver 508 to produce a single echo signal.

The echo signals are communicated to a processing unit 514, which may be implemented by a hardware processor and memory, to process echo signals or images generated from echo signals. As an example, the processing unit 514 can generate additional ultrasound data and/or generate ultrasound images using the methods described in the present disclosure. Images produced from the echo signals by the processing unit 514 can be displayed on a display system 516.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

The present disclosure has described one or more preferred embodiments, and it should be appreciated that many equivalents, alternatives, variations, and modifications, aside from those expressly stated, are possible and within the scope of the invention.

The invention claimed is:

1. A method for localizing a medical device using an ultrasound imaging system, the steps of the method comprising:
   (a) acquiring Doppler signal data representative of a medical device having coupled thereto an active element that is transmitting acoustic energy at an active element excitation frequency while the Doppler signal data are acquired;
   (b) generating with a computer system, time domain data based on the Doppler signal data;
   (c) modulating the time domain data using the active element excitation frequency to create a first resultant modulated signal;
   (d) modulating the time domain data using the active element excitation frequency to create a second resultant modulated signal;
   (e) isolating positive Doppler shifts in the time domain data based on a first combination of the first and second modulated signals using the computer system;
   (f) isolating negative Doppler shifts in the time domain data based on a second combination of the first and second modulated signals using the computer system;
   (g) identifying spatial locations as being associated with a location of the active element by implementing a mean frequency estimator with a hardware processor and a memory of the computer system, wherein the mean frequency estimator takes as an input the isolated positive Doppler shifts and the isolated negative Doppler shifts in the time domain; and
   (h) generating with the computer system, a display that provides a visual depiction of the spatial locations associated with the location of the active element.

2. The method of claim 1, wherein identifying the spatial locations associated with the location of the active element comprises implementing the mean frequency estimator to generate a positive Doppler shift map and a negative Doppler shift map, and wherein the spatial locations are identified based on an intersection of the positive Doppler shift map and the negative Doppler shift map.

* * * * *

UNITED STATES PATENT AND TRADEMARK OFFICE
CERTIFICATE OF CORRECTION

PATENT NO. : 12,343,204 B2  
APPLICATION NO. : 18/188308  
DATED : July 1, 2025  
INVENTOR(S) : Mostafa Fatemi et al.

Page 1 of 1

It is certified that error appears in the above-identified patent and that said Letters Patent is hereby corrected as shown below:

In the Specification

Column 9, Eq. (12), "$X(t)=A_1 e^{j\omega t}+A_2 e^{-\omega t}$" should be --$X(t)=A_1 e^{j\omega t}+A_2 e^{-j\omega t}$--.

Signed and Sealed this  
Sixteenth Day of September, 2025

Coke Morgan Stewart  
*Acting Director of the United States Patent and Trademark Office*